United States Patent
Gonzalez et al.

(10) Patent No.: US 6,488,654 B2
(45) Date of Patent: Dec. 3, 2002

(54) METHOD OF REMOVING MATERIAL FROM A POLYMER TUBE OR CATHETER BALLOON SHAFT

(75) Inventors: Fernando Gonzalez, Campbell, CA (US); Jacky G. Duchamp, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 49 days.

(21) Appl. No.: 09/735,692

(22) Filed: Dec. 12, 2000

(65) Prior Publication Data

US 2002/0072707 A1 Jun. 13, 2002

(51) Int. Cl.$^7$ ............................................. A61M 29/00
(52) U.S. Cl. .................... 604/103.06; 264/138; 216/8
(58) Field of Search .................. 604/103.06, 96.01, 604/264, 103.05, 103.07; 264/255, 259, 139, 148, 162, 400, 138, 159, 161, 163; 216/8, 36, 52, 56

(56) References Cited

U.S. PATENT DOCUMENTS

| | | | | |
|---|---|---|---|---|
| 3,694,280 A | * | 9/1972 | Hoef ............................ | 156/73 |
| 4,321,226 A | * | 3/1982 | Markling .................... | 264/139 |
| 4,384,942 A | | 5/1983 | Glowacki ............... | 204/129.46 |
| 4,753,765 A | * | 6/1988 | Pande .......................... | 264/149 |
| 4,952,357 A | * | 8/1990 | Euteneuer .................... | 264/129 |
| 5,215,614 A | | 6/1993 | Wijkamp et al. ............ | 156/153 |
| 5,334,146 A | * | 8/1994 | Ozasa .......................... | 604/96 |
| 5,525,388 A | * | 6/1996 | Wand et al. ................ | 428/36.9 |
| 5,647,848 A | * | 7/1997 | Jorgensen .................... | 604/96 |
| 5,826,588 A | * | 10/1998 | Forman ........................ | 128/898 |
| 6,168,748 B1 | * | 1/2001 | Wang et al. ................. | 264/520 |
| 6,193,738 B1 | * | 2/2001 | Tomaschko et al. ........ | 606/194 |

\* cited by examiner

Primary Examiner—Charles G. Freay
Assistant Examiner—Han L. Liu
(74) Attorney, Agent, or Firm—Fulwider Patton Lee & Utecht, LLP

(57) ABSTRACT

A method and system for forming a medical device component having a section with a reduced wall thickness, and the device component formed thereby. The method generally comprises rotating a medical device component while a material removal device is placed into contact with a section of the rotating component, to thereby remove material therefrom. In one embodiment, the medical device component is a catheter balloon in which at least one of the proximal and distal shaft sections of the balloon is thinned according to the method of the invention. In another embodiment, the component is a polymeric tube, including polymeric tubes useful in forming a distal tip or catheter shaft section of a catheter.

30 Claims, 4 Drawing Sheets

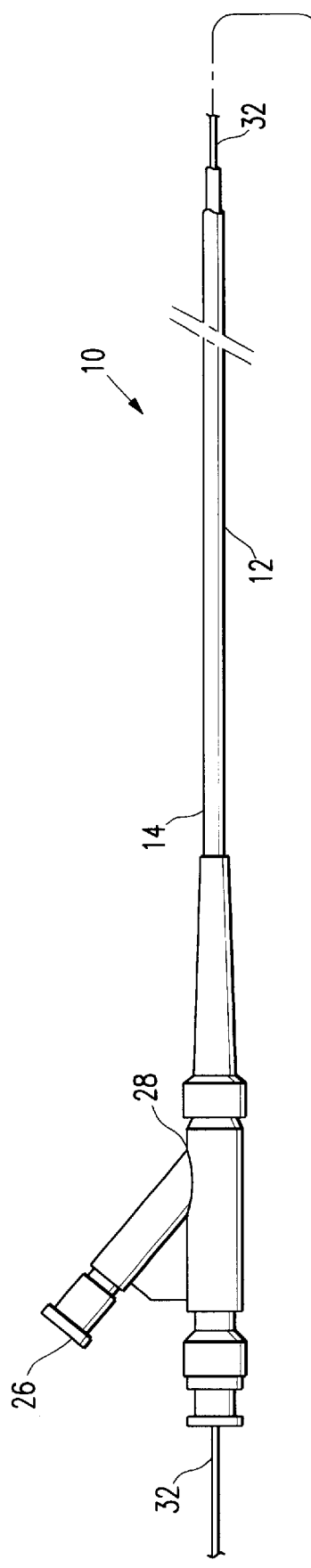
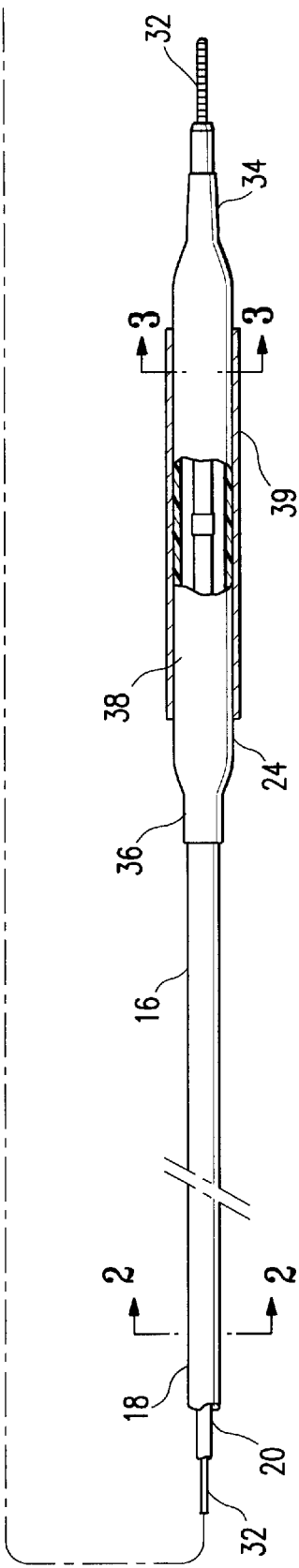
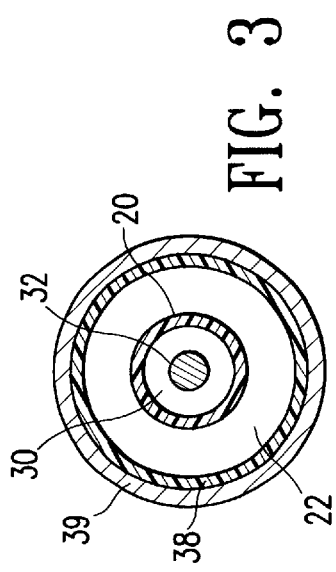
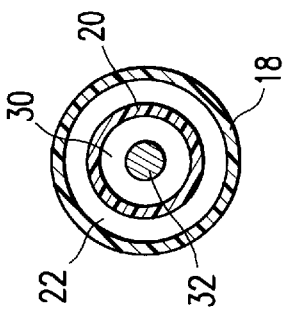
FIG. 1
FIG. 2
FIG. 3

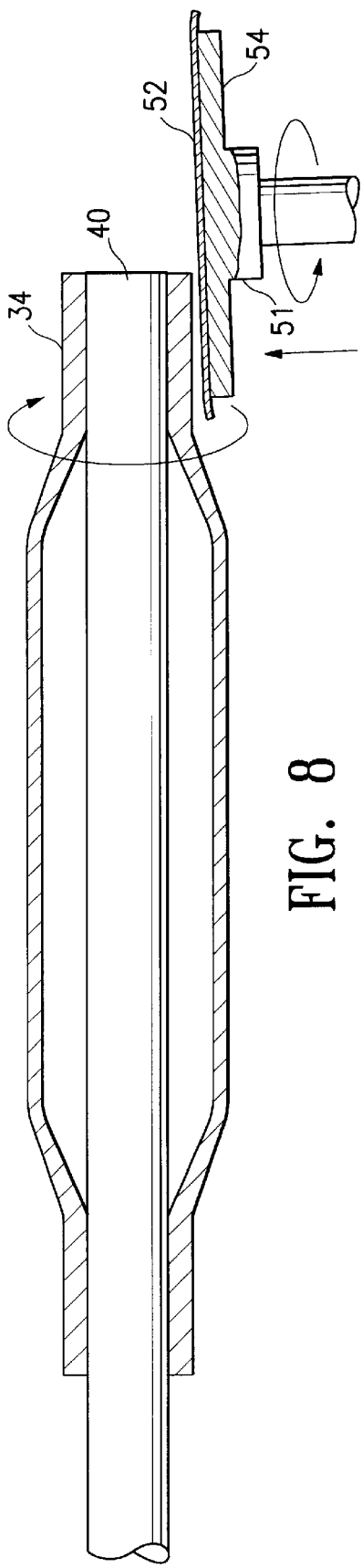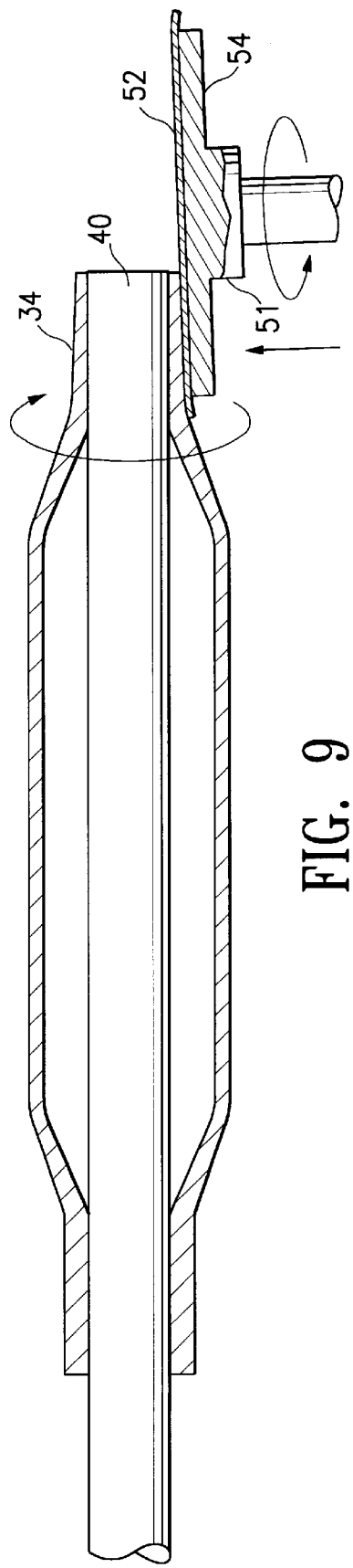

METHOD OF REMOVING MATERIAL FROM A POLYMER TUBE OR CATHETER BALLOON SHAFT

BACKGROUND OF THE INVENTION

This invention generally relates to intravascular catheters, such as balloon catheters used in percutaneous transluminal coronary angioplasty (PTCA).

PTCA is a widely used procedure for the treatment of coronary heart disease. In this procedure, a balloon catheter is advanced into the patient's coronary artery and the balloon on the catheter is inflated within the stenotic region of the patient's artery to open up the arterial passageway and thereby increase the blood flow there through. To facilitate the advancement of the catheter into the patient's coronary artery, a guiding catheter having a preshaped distal tip is first percutaneously introduced into the cardiovascular system of a patient by the Seldinger technique through the brachial or femoral arteries. The guiding catheter is advanced until the preshaped distal tip of the guiding catheter is disposed within the ascending aorta adjacent the ostium of the desired coronary artery, and the distal tip of the guiding catheter is then maneuvered into the ostium. A balloon catheter may then be advanced through the guiding catheter into the patient's coronary artery over a guidewire until the balloon on the catheter is disposed within the stenotic region of the patient's artery.

The balloon is inflated to open up the arterial passageway and increase the blood flow through the artery. Generally, the inflated diameter of the balloon is approximately the same diameter as the native diameter of the body lumen being dilated so as to complete the dilation but not over expand the artery wall. After the balloon is finally deflated, blood flow resumes through the dilated artery and the dilatation catheter can be removed therefrom.

In a large number of angioplasty procedures, there may be a restenosis, i.e. reformation of the arterial plaque in the dilated arterial region. To reduce the restenosis rate and to strengthen the dilated area, physicians now frequently implant an intravascular prosthesis called a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the expanded stent is left in place within the artery.

A low profile, or a small leading outer diameter, is necessary to guide the catheter to the location of the lesion with as little damage to the patient's body lumen as possible. During balloon manufacture, a polymeric tube is formed into a finished balloon having a desired outer diameter and length. The balloon is then placed on the catheter and bonded thereto. Such a manufacturing process may create a step increase in outer diameter from the catheter distal tip to the balloon. The step may create a higher profile, and cause damage and difficulty moving the catheter through the body lumen.

What has been needed is an improved method of forming a thin walled catheter balloon shaft.

SUMMARY OF THE INVENTION

The present invention is directed to a method and system for forming a medical device component having a section with a reduced wall thickness, and the component formed thereby. The method generally comprises rotating a medical device component while a material removal device is placed into contact with a section of the rotating medical device component, to thereby remove material from around the circumference of the section of the component. The material is removed to reduce the overall outer diameter of a section of the component, or form specific configurations such as a threaded section in which the wall thickness is reduced intermittently to thereby form threads. In one embodiment, the medical device component is a catheter balloon in which at least one of the proximal and distal shaft sections of the balloon is thinned according to the method of the invention. In another embodiment, the component is a polymeric tube. Although discussed primarily in terms of a balloon for a catheter, the invention should be understood to include other medical device components, including polymeric tubes useful in forming a distal tip or catheter shaft section of a catheter.

In one embodiment, a catheter balloon comprises a proximal end, a distal end, an expandable section, a proximal shaft section between the proximal end and the expandable section, a distal shaft section between the expandable section and the distal end, and an outer surface. In accordance with a method of the invention, the balloon is placed on a mandrel having a longitudinal axis. The mandrel is rotated around the mandrel longitudinal axis with the balloon on it. A material removal device is positioned to be in contact with an outer surface of at least a section of the rotating balloon to thereby remove balloon material therefrom. The method can also be used on polymeric tube to reduce wall thickness, or form specific configurations such as threaded sections. Such a use would be beneficial if a low profile is needed on a tip of a catheter, or at a junction between two polymeric tubes having similar outer diameters.

The invention is also directed to a medical device component such as a catheter balloon formed according to a method which embodies features of the invention. In one embodiment, the balloon has an expandable section with a wall thickness of about 0.0005 to about 0.002 inches, a distal shaft section having a wall thickness, reduced according to the invention, of about 0.001 to about 0.015 inches, more specifically about 0.002 to about 0.006 inches, and a proximal shaft section having a wall thickness, reduced according to the invention, of about 0.002 to about 0.015 inches, more specifically about 0.002 to about 0.006 inches. The wall thickness of the balloon shaft sections may be greater than or substantially equal to the wall thickness of the expandable section of the balloon. In one embodiment, the proximal shaft section has a wall thickness greater than or equal to the wall thickness of the distal section, and the distal shaft section wall thickness is greater than or equal to the wall thickness of the expandable section. In one embodiment, the shaft sections have a wall thickness about 3 to about 10 times greater than the wall thickness in the expandable section.

The method of the invention provides an improved medical device component having a section with a reduced wall thickness, due to the uniform removal of material. A balloon catheter having a balloon shaft section with a reduced wall thickness according to the invention has improved trackability and crossability. Moreover, the method of the invention does not negatively impact the balloon's rupture and fatigue characteristics. The method of the invention provides for uniform material removal, which thus prevents or lessens the formation of weak spots in the balloon. A thinner wall at the balloon shaft or at a junction will allow for a more flexible transition area from balloon to catheter shaft, or from one polymeric tube to another. The process allows for a reliable, repeatable removal of material, and can be automated to allow for a low cost alternative to removing the material by hand.

BRIEF DESCRIPTION OF THE DRAWINGS

FIG. 1 is an elevational view, partially in section of a catheter embodying features of the invention.

FIG. 2 is a transverse cross sectional view of the catheter of FIG. 1 along line 2—2.

FIG. 3 is a transverse cross sectional view of the catheter of FIG. 1 along line 3—3.

FIG. 8 is an elevational view of the method of the invention with using an alternative embodiment of a system.

FIG. 9 is elevational view of the method of the invention with using an alternative embodiment of a system.

DETAILED DESCRIPTION OF THE INVENTION

Figure 5:
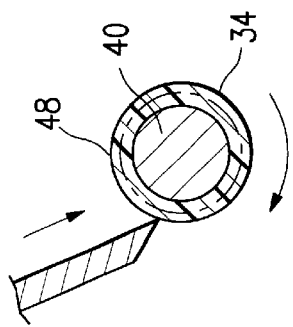
FIG. 5 is a transverse cross sectional view of the method shown in FIG. 4 along line 5—5.
Figure 7:
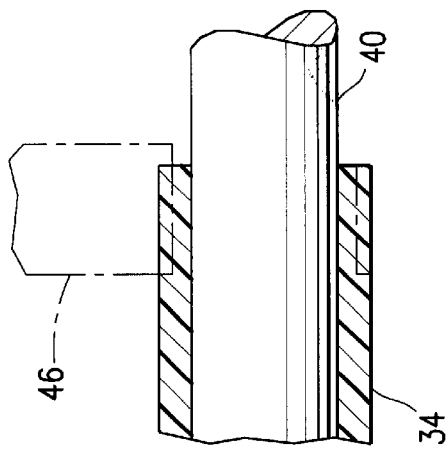
FIG. 7 is a longitudinal cross sectional view of the method shown in FIG. 4 along the line 7—7.

FIGS. 1–3 illustrate a balloon catheter 10 embodying features of the invention. The catheter 10 generally comprises an elongated shaft 12 having a proximal end 14 and a distal end 16. The catheter shaft 12 comprises an outer tubular member 18 and an inner tubular member 20 disposed within the outer tubular member 18 and defining, with the outer tubular member 18, an annular inflation lumen 22. Inflation lumen 22 is in fluid communication with an inflatable balloon 24. Inflation fluid is introduced into the inflation port 26 on the adapter 28, travels through the inflation lumen 22, and inflates the balloon 24. The inner tubular member 20 has an inner lumen 30 extending therein, which is configured to slidably receive a guidewire 32 suitable for advancement through a patient's coronary arteries (see FIGS. 2 and 3, illustrating transverse cross sections of the catheter shown in FIG. 1 taken along lines 2-2 and 3-3, respectively). The distal shaft section 34 of the balloon 24 is sealingly secured to the distal extremity of the inner tubular member 20, and the proximal shaft section 36 of the balloon 24 is sealingly secured to the distal extremity of the outer tubular member 18. The balloon has an expandable section 38 comprising the working section of the balloon. A distal tapered section and a proximal tapered section are at the distal and proximal end, respectively, of the working length of the balloon 24. FIG. 1 illustrates the balloon in an unexpanded configuration. A stent 39 is disposed about a section of the expandable section 38 of the balloon, for delivery and deployment within a patient's body lumen.

Figure 4:
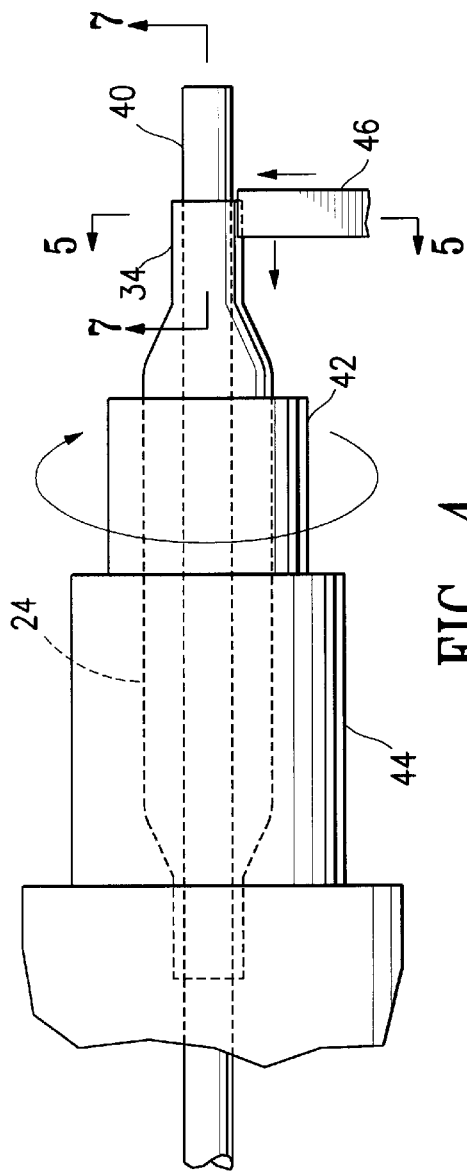
FIG. 4 is an elevational view of the method of the invention with a polymeric balloon, partially in phantom, in the system of the invention.

FIG. 4 illustrates an elevational view, partially in phantom, of a system useful in a method which embodies features of the invention. A polymeric balloon 24 has the distal shaft section 34 which will later be secured to a catheter shaft. The balloon 24 is mounted on a mandrel 40, and the mandrel 40 is mounted in a collet 42 for support. The collet 42 is then drawn into a lathe spindle 44. The spindle 44 is rotatable around a central longitudinal axis of the mandrel 40. In a presently preferred embodiment the spindle is rotated at a speed of about 2500 to about 6000 rpm. The mandrel 40 may be tapered or non-tapered. The mandrel 40 has an outer diameter along at least a length thereof which is essentially equal to the inner diameter of the balloon shaft section 34 or 36 which is being thinned while allowing for the mandrel to be inserted into the lumen of the balloon shaft section.

As the lathe spindle 44 rotates about the mandrel 40 longitudinal axis, the balloon 24 mounted on the mandrel 40 also rotates. A turning tool (not shown) then brings a material removal device 46 in contact with an outer wall 48 of the rotating balloon 24. The turning tool may move either the rotating balloon 24 or the material removal device 46, or both until they are in contact. The material removal device 46 may be a number of devices known in the art, including a laser and beam, a chemical solvent, a grinding wheel or an abrasive surface. In the embodiment illustrated in FIGS. 4 and 5, the material removal device 46 is a sharp edged cutting tool configured to mechanically cut material from an outer surface 48 of the balloon 24, so that the material removal device 46 is moved into contact with the balloon shaft section 34 to thereby cut down to the desired thickness. FIG. 5 illustrates a transverse cross section of the system shown in FIG. 4 taken along line 4—4, with the material removal device 46 in contact with the balloon outer surface 48. The material removal device 46 may be placed at a determined distance from the mandrel 40 to effect a desired wall thickness on the balloon shaft section 34 or 36 being thinned. With the material removal device 46 remaining a set distance from the rotating mandrel 40, the material is removed uniformly, to thereby result in a uniform wall thickness in the reduced diameter section of the balloon. In one embodiment, the reduced outer diameter of the distal shaft section 34 is about 0.025 to about 0.035, for a 3.0 mm inflated outer diameter balloon.

The rotating mandrel 40 causes the material to be removed from the entire circumference of the outer wall 48 of the balloon shaft 34. In one embodiment, the material removal device 46 and the balloon shaft section 34 are longitudinally displaced with respect to one another during material removal. This allows the material removal device 46 to remove material along the outer wall 48 for a desired length along the shaft section 34. In one embodiment, the length along which material is removed is about 0.5 to about 4 mm. Once the material has been removed in the length and thickness necessary for the purposes of the user, the material removal device 46 is removed from contact with the balloon shaft section 34, and the mandrel 40 ceases rotation. The balloon 24 may then have the same process done to the opposite shaft section 36. Once the balloon is complete, it is removed from the mandrel 40 and secured to a catheter shaft 10.

Figure 6:
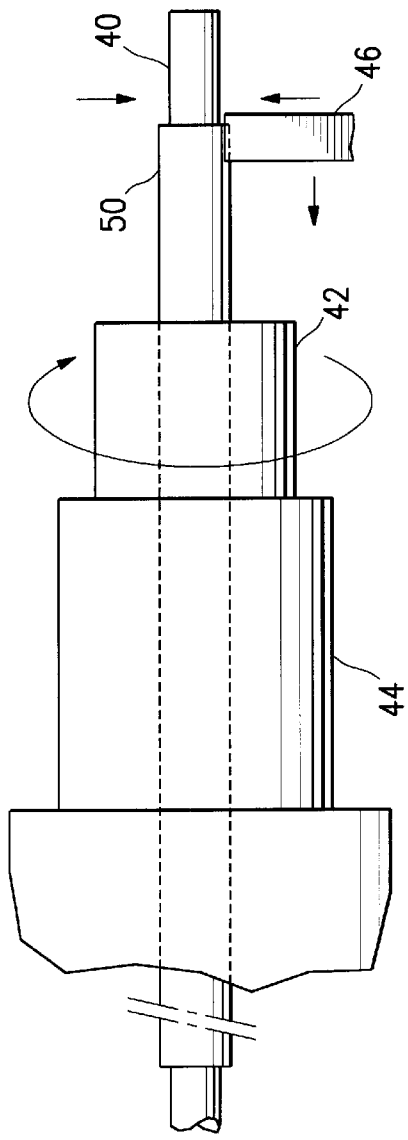
FIG. 6 is elevational view of the method of the invention with a polymeric tube, partially in phantom, in the system of the invention.

The process may additionally be used to thin the wall of a polymeric tube 50 as shown in FIG. 6. This would be beneficial if the tube 50 needs a thin entry profile. Additionally, it may be necessary to thin the wall of a tube 50 to facilitate the joining of that tube with another tube having similar outer and inner diameters. The process can be used to remove about 10% to about 70%, preferably about 50% of the material from either a polymer tube 50 or a balloon shaft section 34, resutling in a uniform wall thickness section with good flexibility, bondability ,and a low profile.

FIGS. 8 and 9 illustrate a system, partially in section, which embodies features of the invention, having an abrasive surface material removal device 51. The material removal device 51 has an abrasive surface 52. In one embodiment the abrasive surface comprises a sandpaper-like grain of about 9 um to about 30 um. The abrasive surface 52 is preferably a circular form having a diameter of about 1 to about 3 cm. The abrasive surface 52 rotates around an axis which is generally perpendicular to the longitudinal axis of the mandrel. The abrasive surface 52 is secured to a plate 54. The plate 54 has a diameter which may be smaller than the diameter of the abrasive surface 52. In embodiments having the smaller plate diameter, the balloon shaft section 34 may have a more tapered wall thickness. In one embodiment, after removal of material using first abrasive surface 52, the abrasive surface 52 is replaced with another abrasive surface (not shown) having a finer abrasive surface of, for example, about 1 um to about 9 um, to produce a smoother outer surface.

The method may include cleaning the resulting balloon shaft 34 or polymeric tube 52. In certain embodiments, the material removal device 46 may leave material deposits on the newly formed outer wall. These must be removed before insertion into a patient. The shaft may be cleaned with a cleaning solvent, such as isopropyl alcohol. A preferred embodiment of the invention would not leave any material deposits, such as when the material removal device 46 is the sharp edge cutting tool, because the friction of the cutting tool against the polymeric tube or balloon shaft melts all debris into the new outer wall formed after the material removal.

Figure 10:
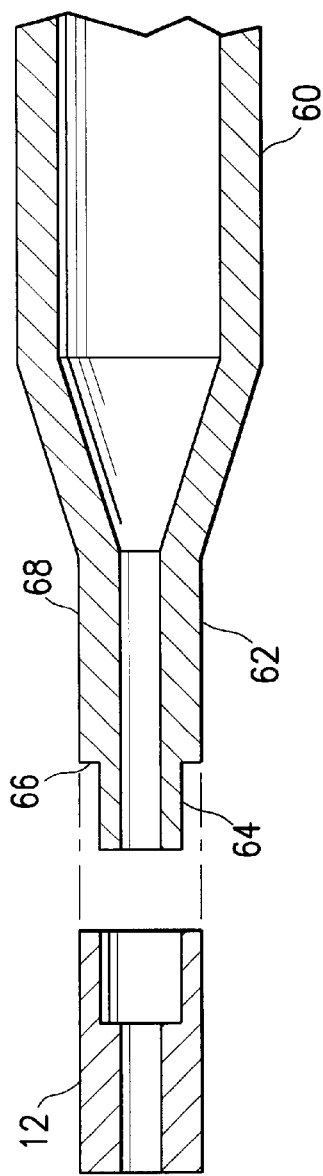
FIG. 10 is a longitudinal cross sectional view of a section of a balloon formed according to a method which embodies features of the invention, having a balloon shaft section with a reduced wall thickness section and an abrupt transition to a larger diameter portion of the balloon shaft section.
Figure 11:
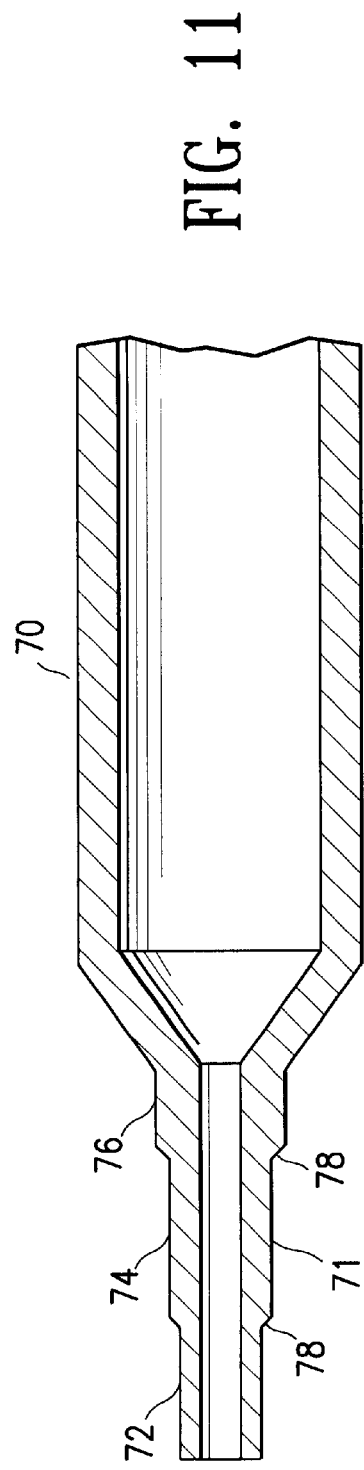
FIG. 11 is a longitudinal cross sectional view of a section of a balloon formed according to a method which embodies features of the invention, having a balloon shaft section with a reduced wall thickness section and tapered transitions to a larger diameter portion of the balloon shaft section.
Figure 12:
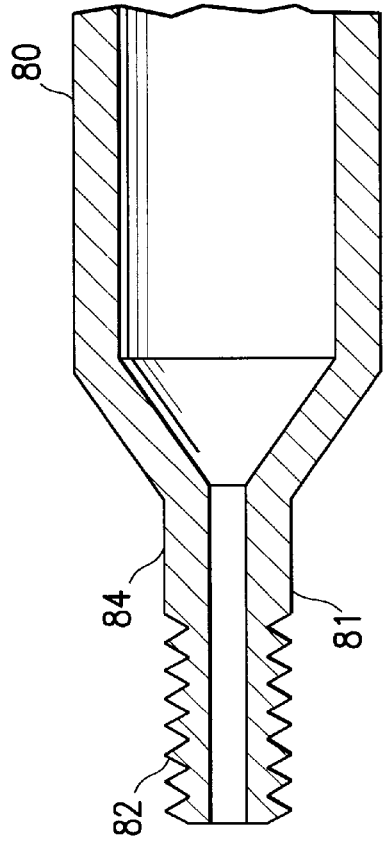
FIG. 12 is a longitudinal cross sectional view of a section of a balloon formed according to a method which embodies features of the invention, having a balloon shaft section with threaded portion.

FIGS. 10–12 illustrate specific configurations of a section of a balloon from which material has been removed according to a method which embodies features of the invention. FIG. 10 is a longitudinal cross sectional view of a section of a balloon 60 formed according to a method which embodies features of the invention, having a stepped diameter balloon shaft section 62 with a reduced wall thickness portion 64 and an abrupt transition 66 to a larger diameter portion 68 of the balloon shaft section. A catheter shaft 12 has a section configured to mate with the reduced diameter portion 64, to form a lap joint therebetween. FIG. 11 is a longitudinal cross sectional view of a section of a balloon 70 formed according to a method which embodies features of the invention, having a stepped diameter balloon shaft section 71 with a first reduced wall thickness section 72 having a smaller outer diameter than a second reduced wall thickness section 74, and tapered transitions 78 to a larger diameter portion 76 of the balloon shaft section. In a preferred embodiment, the tapered transitions 78 taper at a 45 degree angle. FIG. 12 is a longitudinal cross sectional view of a section of a balloon 80 formed according to a method which embodies features of the invention, having a balloon shaft section 81 with threaded portion 82 and a nonthreaded portion 84. In one embodiment, the threaded portion 82 is formed by cutting the material from the balloon shaft section according to a method embodying features of the invention as discussed above.

The catheter 10 illustrated in FIG. 1 is an over-the-wire catheter, however any type of catheter may benefit from the invention including a rapid exchange catheter, stent delivery catheter, and catheters configured for peripheral or neurological uses. Rapid exchange catheters generally comprise a distal guidewire port, a proximal guidewire port spaced a short distance from the distal end of the catheter and a substantially greater distance from the proximal end of the catheter, and a short guidewire lumen extending between the distal and proximal guidewire ports.

The invention has been described in terms of certain preferred embodiments, and those of skill in the art will recognize that certain modifications can be made without departing from the scope of the invention. Although individual features of embodiments of the invention may be shown in some of the drawings and not in others, those skilled in the art will recognize that individual features of one embodiment of the invention can be combined with any or all the features of another embodiment.

What is claimed is:

1. A method of forming a catheter balloon, comprising:
   a) providing a balloon formed of a material having a proximal end, a distal end, an expandable section, a proximal shaft section between the proximal end and the expandable section, a distal shaft section between the expandable section and the distal end, and an outer surface;
   b) placing the balloon on a mandrel having a longitudinal axis and rotating the mandrel around the mandrel longitudinal axis to rotate the balloon thereon; and
   c) positioning a material removal device in contact with an outer surface of at least a section of the rotating balloon to thereby remove balloon material from a portion of at least one of the proximal shaft section and the distal shaft section to form a stepped diameter shaft section having a first portion with a substantially uniform first diameter and a second portion with a substantially uniform second diameter, different than the first diameter.

2. The method of claim 1 wherein the section of the rotating balloon is the proximal shaft section, and including causing relative longitudinal displacement between the balloon and the material removal device to remove balloon material from a length of the proximal shaft section.

3. The method of claim 1 wherein the section of the rotating balloon is the distal shaft section, and including causing relative longitudinal displacement between the balloon and the material removal device to remove balloon material from a length of the distal shaft section.

4. The method of claim 1 wherein the material removal device is a sharp edge cutting tool and (c) comprises mechanically cutting balloon material to remove the balloon material.

5. The method of claim 1 wherein the material removal device is a rotating disk having an abrasive surface with a first grain value and (c) comprises abrasively removing balloon material.

6. The method of claim 5 wherein the rotating disk has a diameter larger than a width of the section of the rotating balloon, and (c) comprises removing the same amount of material at any point around the circumference of the section of the rotating balloon.

7. The method of claim 5 wherein the rotating disk comprises a circular plate having a radius, the abrasive surface has a radius greater than the radius of the circular plate and an adhesive securing the abrasive surface to the circular plate and (c) comprises abrasively removing the balloon material.

8. The method of claim 5, wherein (c) further comprises:
providing at least one additional disk having a second grain value less than the first grain value of the rotating disk; and
removing additional material from the balloon with the additional disk.

9. The method of claim 1 wherein the material removal device comprises at least one rotating grinding wheel and (c) comprises grinding the section of the rotating balloon to remove the balloon material.

10. The method of claim 1 wherein the material removal device is a laser emitting device and the laser beam produced by the laser emitting device and (c) includes burning the balloon material to remove the balloon material.

11. The method of claim 1 wherein the material removal device is a chemical solvent and (c) comprises causing a chemical reaction in an outer surface of the balloon material to remove the balloon material.

12. The method of claim 1 further comprising after (c) cleaning the balloon of all material deposits resulting from the material removal.

13. The method of claim 1 further comprising, during (c) melting all material deposits into a new outer surface of the balloon concurrently with the removal of material.

14. The method of claim 1 further comprising cutting the balloon to a desired length.

15. The method of claim 1 wherein (c) includes removing material along a length of about 0.05 mm to about 5 mm of the balloon.

16. The method of claim 1 wherein the section of the rotating balloon has a wall thickness, and (c) includes reducing the wall thickness by about 10% to about 70%, so that the section of the rotating balloon has a reduced wall thickness substantially equal to the wall thickness of the expandable section of the balloon.

17. The method of claim 1 wherein the stepped diameter shaft section comprises an abrupt transition between the first diameter portion and the second diameter portion of the shaft section configured for forming a lap joint with a catheter shaft.

18. The method of claim 1 wherein the stepped diameter shaft section comprises a tapered transition between the first diameter portion and the second diameter portion of the shaft section.

19. The method of claim 18 including forming two or more tapered transitions having a tapering angle of about 45 degrees.

20. The method of claim 1 wherein the stepped diameter shaft section comprises a threaded portion.

21. A method of forming a thin walled polymeric tube for use as a medical device component, comprising:
a) providing a polymeric tube formed of a material having a proximal end, a distal end, at least one lumen therethrough, and an outer surface;
b) placing the polymeric tube on a mandrel having a longitudinal axis and rotating the mandrel and the polymeric tube thereon around the mandrel longitudinal axis; and
c) positioning a material removal device in contact with an outer surface of at least a section of the polymeric tube to thereby remove polymeric material from a portion of at least one of the proximal end and the distal end to form a stepped diameter section having a first portion with a substantially uniform first diameter and a second portion with a substantially uniform second diameter, different than the first diameter.

22. A system for removing material from a polymer tube to form a medical device component having a stepped diameter shaft section having a first portion with a substantially uniform first diameter and a second portion with a substantially uniform second diameter, different than the first diameter, said system comprising:
a) a mandrel having a longitudinal axis, a first end and a second end;
b) a collet having a gripping end and a second end, the gripping end gripping the first end of the mandrel;
c) a lathe spindle secured to the second end of the collet;
d) a polymer tube having a longitudinal axis, a first end, a second end and a lumen therethrough, disposed about the second end of the mandrel;
e) a material removal device configured to remove material from an end of the polymeric tube; and
f) a turning tool secured to the material removal device and configured to move the material removal device between first and second locations relative to the mandrel such that material forming the polymer tube may be removed by the material removal device to form the first and second portions of the stepped diameter shaft section.

23. The system of claim 22 wherein the polymer tube is an inflatable balloon.

24. The system of claim 22 wherein the mandrel has an external taper along the longitudinal axis.

25. The system of claim 22 wherein the material removal device is a sharp edge cutting tool.

26. The system of claim 22 wherein the material removal device is a rotating abrasive surface.

27. The system of claim 22 wherein the material removal device is a grinding wheel.

28. The system of claim 22 wherein the material removal device is a laser and beam.

29. The system of claim 22 wherein the material removal device is a chemical solvent.

30. A catheter balloon, comprising an expandable section having a wall thickness, a proximal shaft section having a wall thickness, and a distal shaft section, having a wall thickness, wherein the wall thickness of the proximal and distal shaft sections are about 3 to about 10 times greater than the expandable section wall thickness and at least one of the proximal shaft section and the distal shaft section have a stepped diameter shaft section having a first portion with a substantially uniform first diameter and a second portion with a substantially uniform second diameter, different than the first diameter.

* * * * *